US 6,669,655 B1

(12) United States Patent
Acker et al.

(10) Patent No.: US 6,669,655 B1
(45) Date of Patent: Dec. 30, 2003

(54) SONIC ELEMENT AND CATHETER INCORPORATING SAME

(75) Inventors: David E. Acker, Setauket, NY (US); Alfred Novak, Miami, FL (US)

(73) Assignee: Transurgical, Inc., Setauket, NY (US)

( * ) Notice: Subject to any disclaimer, the term of this patent is extended or adjusted under 35 U.S.C. 154(b) by 184 days.

(21) Appl. No.: 09/691,825

(22) Filed: Oct. 19, 2000

Related U.S. Application Data

(60) Provisional application No. 60/173,533, filed on Dec. 29, 1999, and provisional application No. 60/160,546, filed on Oct. 20, 1999.

(51) Int. Cl.[7] ................................................ A61H 1/00
(52) U.S. Cl. .................................................... 601/2
(58) Field of Search ...................... 601/2, 3, 4; 600/437, 600/439, 459, 462, 466, 470, 471; 607/96, 98, 99

(56) References Cited

U.S. PATENT DOCUMENTS

| | | | | |
|---|---|---|---|---|
| 4,087,716 A | * | 5/1978 | Heywang ..................... | 310/332 |
| 4,205,686 A | * | 6/1980 | Harris et al. ................ | 600/459 |
| 5,069,664 A | * | 12/1991 | Guess et al. .................. | 604/22 |
| 5,099,702 A | * | 3/1992 | French ..................... | 73/862.68 |
| 5,111,805 A | * | 5/1992 | Jaggy et al. ..................... | 601/4 |
| 5,316,000 A | * | 5/1994 | Chapelon et al. ........... | 600/439 |
| 5,380,274 A | * | 1/1995 | Nita ............................. | 604/22 |
| 5,471,988 A | | 12/1995 | Fujio et al. .................. | 128/660 |
| 5,630,837 A | | 5/1997 | Crowley | |
| 5,735,811 A | * | 4/1998 | Brisken ........................ | 604/22 |
| 5,762,066 A | * | 6/1998 | Law et al. ................... | 600/439 |
| 5,840,031 A | | 11/1998 | Crowley | |
| 6,361,500 B1 | * | 3/2002 | Masters ....................... | 600/466 |
| 6,413,254 B1 | * | 7/2002 | Hissong et al. ............... | 606/27 |

FOREIGN PATENT DOCUMENTS

WO    WO 99/02096    1/1999

\* cited by examiner

*Primary Examiner*—Sang Paik
(74) *Attorney, Agent, or Firm*—Lerner, David, Littenberg, Krumholz & Mentlik, LLP

(57) ABSTRACT

A catheter carrying a radially-expansible ultrasonic transducer is threaded into the circulatory system and then the transducer is actuated to provide ultrasonic energy in a ring-like zone surrounding a blood vessel. Desirably, the transducer is arranged to focus the ultrasonic energy into a narrow, ring-like focal zone having an extent, in the axial direction along the catheter, less than the axial extent of the transducer. The transducer desirably is expanded after threading so that during application of the ultrasonic energy, the transducer bears on the interior wall of a blood vessel through a balloon covering the transducer. The transducer may include one or more resilient spiral elements carrying a flexible piezoelectric material.

14 Claims, 7 Drawing Sheets

SONIC ELEMENT AND CATHETER INCORPORATING SAME

CROSS REFERENCE TO RELATED APPLICATIONS

The present application claims benefit of U.S. Provisional Patent Applications No. 60/173,533, filed Dec. 29, 1999 and 60/160,546, filed Oct. 20, 1999, the disclosure of which is hereby incorporated by reference herein.

FIELD OF THE INVENTION

The present invention relates to sonic emitting elements, to catheters incorporating the same and to methods of treating tissue in the body of a subject using such elements on catheters.

BACKGROUND OF THE INVENTION

As described in International Publication WO 99/02096, the disclosure of which is hereby incorporated by reference herein, certain cardiac arrhythmias can be treated by ablating tissue in a ring around a pulmonary vein at the juncture between the pulmonary vein and the heart. As described in the '096 publication, such ablation can be performed by threading a catheter having a thermal ablation element at its distal tip into the heart so that the tip is lodged within the appropriate pulmonary vein. The catheter may bear a balloon which is inflated within the vein and which holds the catheter in place. The ablating element is then actuated so as to apply heat in a region surrounding the ablating element. In certain embodiments taught in the '096 publication, the ablating element includes a radio frequency ("RF") emitting antenna.

Other embodiments described in the '096 publication disclose the use of ultrasonic transducers. The ultrasonic transducer can be actuated to apply sonic energy through a fluid contained in the balloon, thereby heating the tissue surrounding the balloon. The preferred ultrasonic transducer illustrated in the '096 publication is a ceramic piezoelectric element in the form of an elongated hollow tube having two cylindrical electrodes on its covering inner and outer surfaces. The entire piezoelectric element is excited by an alternating voltage and emits generally cylindrical sonic pressure waves.

Such a cylindrical transducer can apply only limited levels of power within a given volume of tissue. The '096 publication suggests that a power level of 20 watts per centimeter of length along the vessel is adequate for ablation. While it is at least theoretically possible to heat tissues to a degree sufficient to cause ablation using relatively low power levels per unit of volume, such low-level heating prolongs the time required to heat the tissue. This, in turn, increases heat conduction from the heated tissues and increases the risk that adjacent tissue will suffer heat damage.

As also explained in the '096 publication, such a cylindrical transducer typically must have an axial length at least equal to the wavelength of the sound in the transducer material. Accordingly, such a transducer tends to ablate tissue along a significant length of the pulmonary vein. This is undesirable because the desired treatment only requires ablation of a short ring of tissue surrounding the pulmonary vein to interrupt an undesired electrical conduction path. To avoid this undesirable result, the '096 publication suggests masking the emissions from the ends of the cylindrical ultrasonic element. Such masking wastes the sonic power from the transducer, thus further aggravating the problem of providing adequate heating.

As a further alternative, the '096 publication shows an ultrasonic emitter in the form of a hollow concave disk. The '096 publication suggests that such an emitter can be physically rotated around the axis of a catheter so as to ablate a ring-like zone. This approach entails considerable practical difficulties inasmuch as entire rotatable assembly must be made to fit into a catheter which can be threaded through the circulatory system of the patient and into the pulmonary veins, typically a catheter having a diameter no more than a few mm.

Thus, despite all of the efforts devoted heretofore to development of procedures for ablating a circular region around a blood vessel, there are still substantial needs for further improvements.

SUMMARY OF THE INVENTION

The present invention addresses these needs. One aspect of the invention provides methods of ablating or otherwise treating tissues. A method according to this aspect of the invention desirably includes the step of threading a catheter into the circulatory system of the subject so that an emitting element carried on the catheter is positioned within a circulatory vessel with a central axis of the emitting element substantially aligned with an axis of the circulatory vessel. The emitting element is actuated to emit sonic energy in a pattern which is generally symmetrical about its central axis. The sonic energy is emitted so that the sonic waves from different portions of the emitting element intersect and mutually reinforce one another in a ring-like focal region surrounding the central axis, said focal region has an axial length less than the axial length of the emitting element. For example, sonic energy from different portions of the emitting element along the axial extent of emitting element may be directed at different angles to the central axis of the emitting element. Alternatively or additionally, sonic energy from different portions of the emitting element along the axial extent of emitting element may be emitted with different phases.

A further aspect of the present invention provides a sonic emitting element incorporating a piezoelectric element having a radiating surface substantially in the form of a surface of revolution generated by rotating a generatrix about a central axis. The term "generatrix" as used in this disclosure refers to a line or curve. The generatrix desirably includes a minimum point at a minimum distance from the central axis, and includes a first portion sloping away from the central axis in a first axial direction along the central axis from the minimum point. Desirably, the generatrix includes a second portion sloping away from the central axis in a second axial direction from the minimum point. The first and second portions of the generatrix desirably are curved and most preferably the first and second portions of the generatrix are segments of a circle. Thus, the radiating surface is in the form of an outwardly-facing concave portion of a toroidal surface.

The transducer may include one or more radially-expansible elements such as resilient spiral elements carrying a piezoelectric material such one or more layers of a polymeric piezoelectric film, together with electrodes used to actuate the film. Further aspects of the invention provide catheters incorporating sonic elements as discussed above.

DETAILED DESCRIPTION OF THE PREFERRED EMBODIMENTS

Figure 1:
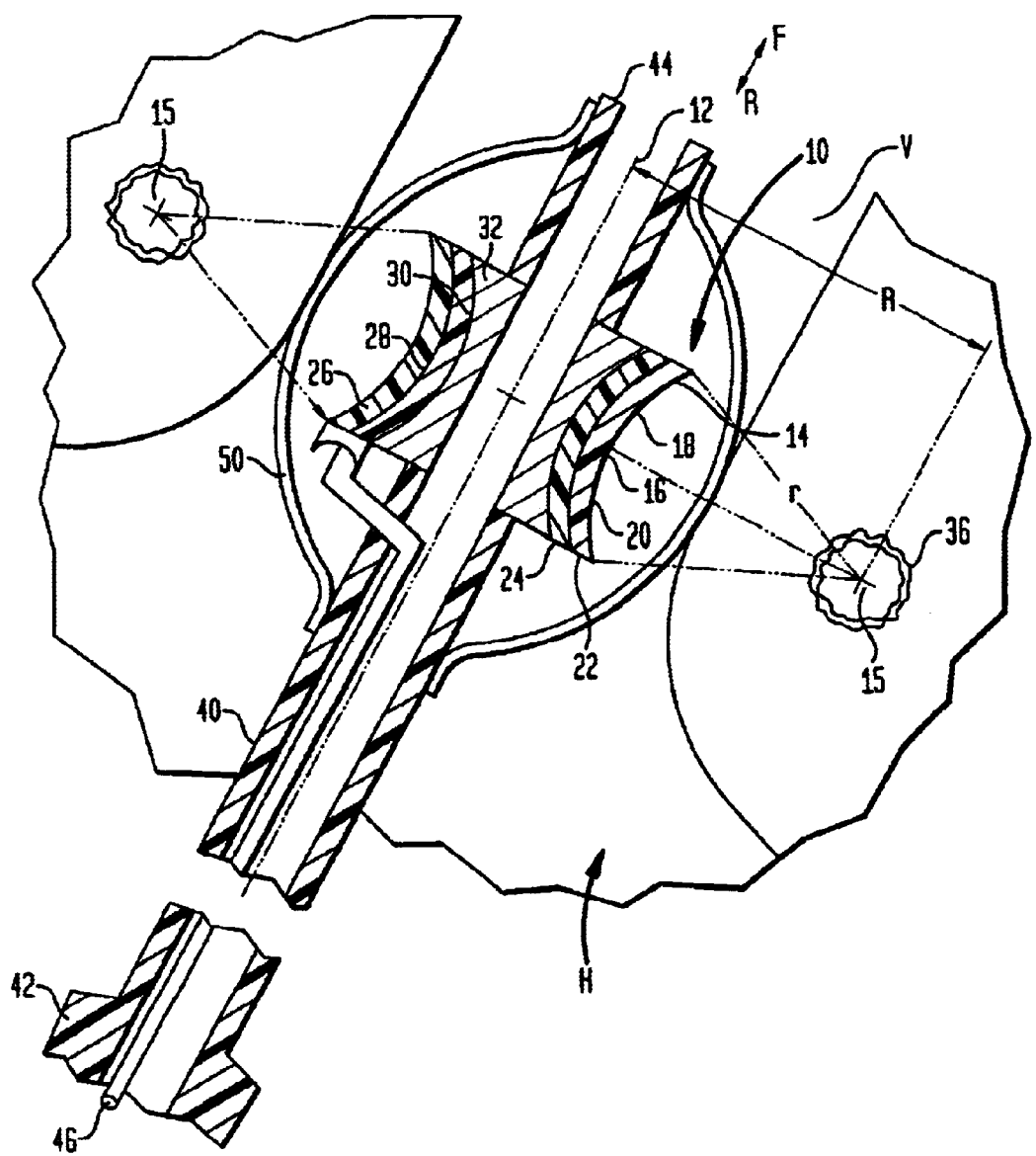
FIG. 1 is a diagrammatic sectional view depicting a catheter in accordance with one embodiment of the invention in conjunction with certain tissues of a subject being treated.

As seen in FIG. 1, a polymeric piezoelectric element 10 has a central axis 12 and an outer, radiating surface 14. The radiating surface is in the form of a surface of revolution formed by a generatrix in the form of an arc having radius r and a center 15 disposed at radius R from axis 12, this arc being swept around central axis 12. Thus, the generator or arc has a minimum point 16 adjacent the axis, a first portion 18 curving away from the central axis in a forward longitudinal direction f along central axis 12 (upwardly and to the right as seen in FIG. 1) along central axis 12 and having a second portion 20 curving away from the central axis 12 in a second axial direction (downwardly and to the left in FIG. 1). Those portions of radiating surface 14 lying in the first portion face in the second or rearward axial direction, whereas those portions of surface 14 lying in the second portion 20 face in the forward or first axial direction F.

The piezoelectric element 10 most preferably is formed from a polymeric piezoelectric material such as polyvinylidene fluoride (PVDF) or a piezoelectric ceramic or composite material such as those commonly known as PZT-8 or PZT-4 and has at least two electrodes positioned so that piezoelectric material lies between the two electrodes. The particular transducer illustrated in FIG. 1 is a multi-layer transducer incorporating a plurality of individual piezoelectric layers 22, 24 and electrodes 26, 28, 30 interspersed with the polymeric layers. The polymeric layers are superposed on a rigid base 32 such as ceramic or metallic element. The outer surface of base 32 desirably also is in the form of a surface of revolution about central axis 12. As described in greater detail in the co-pending commonly assigned U.S. provisional application No. 60/125,676, the disclosure of which is hereby incorporated by reference herein, it is most desirable to provide the piezoelectric transducer incorporating at least two layers of piezoelectric materials such as piezoelectric polymer and at least three electrodes, the layers of piezoelectric material being superposed on one another so that each layer of piezoelectric material is disposed between two of the electrodes. In the particular embodiment illustrated in FIG. 1, piezoelectric layer 24 is disposed between electrodes 28 and 30 whereas layer 22 is disposed between electrodes 26 and 28. Most preferably, electrode 28 serves as a "hot" or signal electrode, whereas electrodes 26 and 30 are grounded. The piezoelectric materials are arranged so that sonic vibrations from the two layers reinforce one another when an alternating signal is applied at electrode 28.

As will be appreciated with reference to FIG. 1, application of an alternating potential on electrode 28 causes the emitting surface 14 to vibrate at the frequency of the applied potential. Thus, sonic waves will be emitted from all sections of emitting surface 14. The sonic waves from the entire emitting surface reinforce one another in a ring-like region 36 centered on a circle corresponding to the theoretical ring swept by the center 15 of the generatrix of surface 14. Because of such reinforcement, the intensity of the sonic waves will be far higher in this ring-like region 36 than in other areas.

The emitting element discussed above desirably is mounted on an elongated catheter body 40 having a proximal end 42 and a distal end 44. The emitting element may be mounted remote from the proximal end and desirably adjacent the distal end of the catheter body. The catheter is provided with conductors 46 connected to the electrodes of the piezoelectric element. These conductors may be connected to a conventional high frequency generator for driving the piezoelectric element. The catheter may also include a balloon 50 similar to the balloon discussed in the '096 publication. Such a balloon may be filled with water or other ultrasonic-transmitting medium so as to couple the sonic emissions from the transducer into the surrounding tissues.

In a method according to a further aspect of the invention, the distal end 44 of the catheter is advanced through the circulatory system of the patient into a pulmonary vein V so that the balloon 50 and emitting element 10 are disposed in the vein adjacent to the juncture of the vein and the heart chamber H. Balloon 50 is inflated with water or other ultrasonic transmitting medium and bears against the inner wall of the vein. The piezoelectric element is actuated so as to heat the tissue in a ring-like region 36 surrounding the emitting element. Desirably, such heating is accomplished rapidly, within about 500 milliseconds. The ring-like element 36 is depicted in FIG. 1 as lying inside the tissue, remote from the wall of the vein V. However, in practice the ring-like ablated region can be located at any distance from the central axis 12 of the emitting element depending upon the curvature and dimensions of surface 14. For example, the ablated region may lie on the surface of the vein wall.

In the method and apparatus discussed above, the piezoelectric element provides strong exitation, and can be readily formed into the shape desired as, for example, into a body of revolution about the central axis. The piezoelectric material thus greatly facilitates fabrication of transducers in the relatively small sizes, desirably less than about 1 cm and most desirably less than about 2 mm in diameter suitable for threading into the circulatory system of a human or other mammalian subject. The piezoelectric films can be wound or wrapped around the central support 32 to form the emitting element. As described in the aforementioned co-pending, commonly assigned patent application, the electrodes used on the piezoelectric films can be provided as printed conductive areas. For these and other reasons, the use of piezoelectric films is preferred. One particular PVDF piezoelectric material suitable for use in practice of the present invention is available from Measurement Specialties, Inc. of Norristown, Pa., United States of America.

Figure 2:
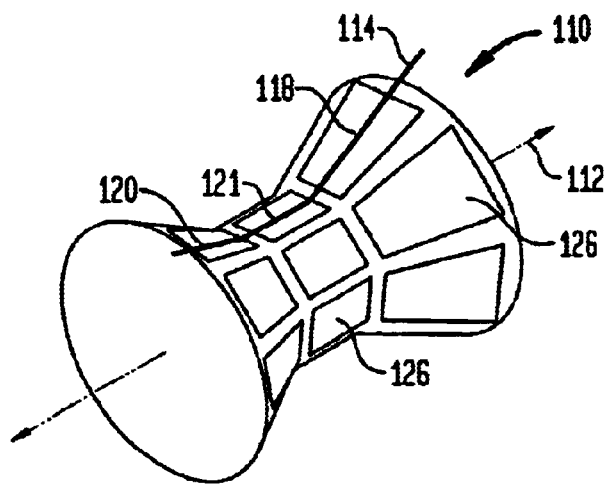
FIG. 2 is a diagrammatic perspective view depicting an emitting element in accordance with a further embodiment of the invention.

Apparatus according to a further embodiment of the invention (FIG. 2) incorporates a piezoelectric structure generally in the form of a body of revolution about a central axis 112 having a generatrix 114 with a first straight sloping portion 118, a second straight sloping portion 120 and an intermediate portion 121 at a constant distance from the central axis 112. Thus, the emitting surface is generally in the form of a pair of frustoconical bodies having their narrow ends facing towards one another and joined by a cylinder. Also, the emitting surface in this embodiment does not lie exactly on the surface of revolution but instead includes discrete, flat panels 126 which cooperatively approximate the surface of revolution formed by generatrix 114. Here again, if all of the elements are driven in phase, sonic waves emitted by the various elements will reinforce one another generally at a ring-like region surrounding the central axis 112.

In a further embodiment, the transducer has a substantially cylindrical radiating surface divided into a plurality of bands 222, 223, 224 spaced axially along central axis 212. The piezoelectric material in each of these bands is provided with a separate set of electrodes. For example, the piezoelectric material in band 222 is associated with an inner electrode 201 and an outer electrode 203. A similar, separate set of inner and outer electrodes is provided for each of the other bands. The separate sets of electrodes are connected to the leads 240 extending through the catheter so that separate exitation signals may be applied to each band. For example, the outer electrode of each set may be a ground electrode, and all of the ground electrodes may be connected to a common lead, whereas separate "hot" connections extend to the opposing inner electrodes. In operation, the various bands of piezoelectric material are excited out of phase with one another, with the end bands 222 and 224 in phase-leading relation with the central band 223. Here again, the sonic waves from the various bands will constructively reinforce one another at a ring-like region surrounding axis 212.

Figure 4:
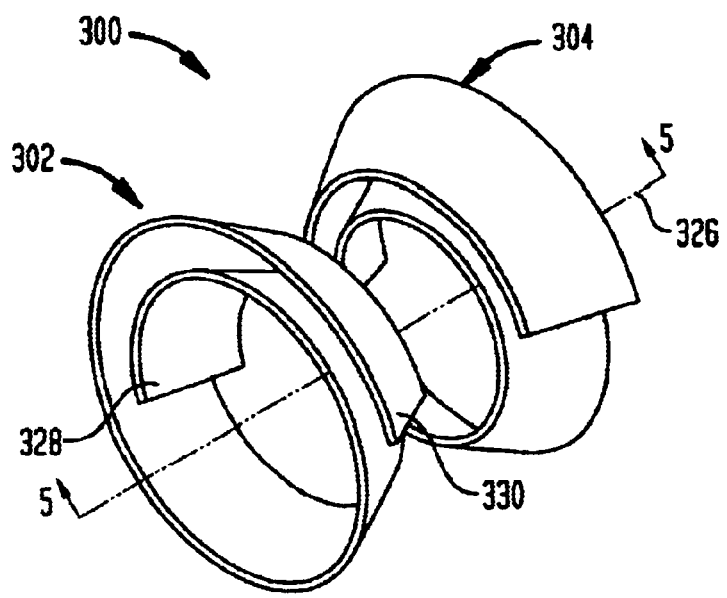
Figure 5:
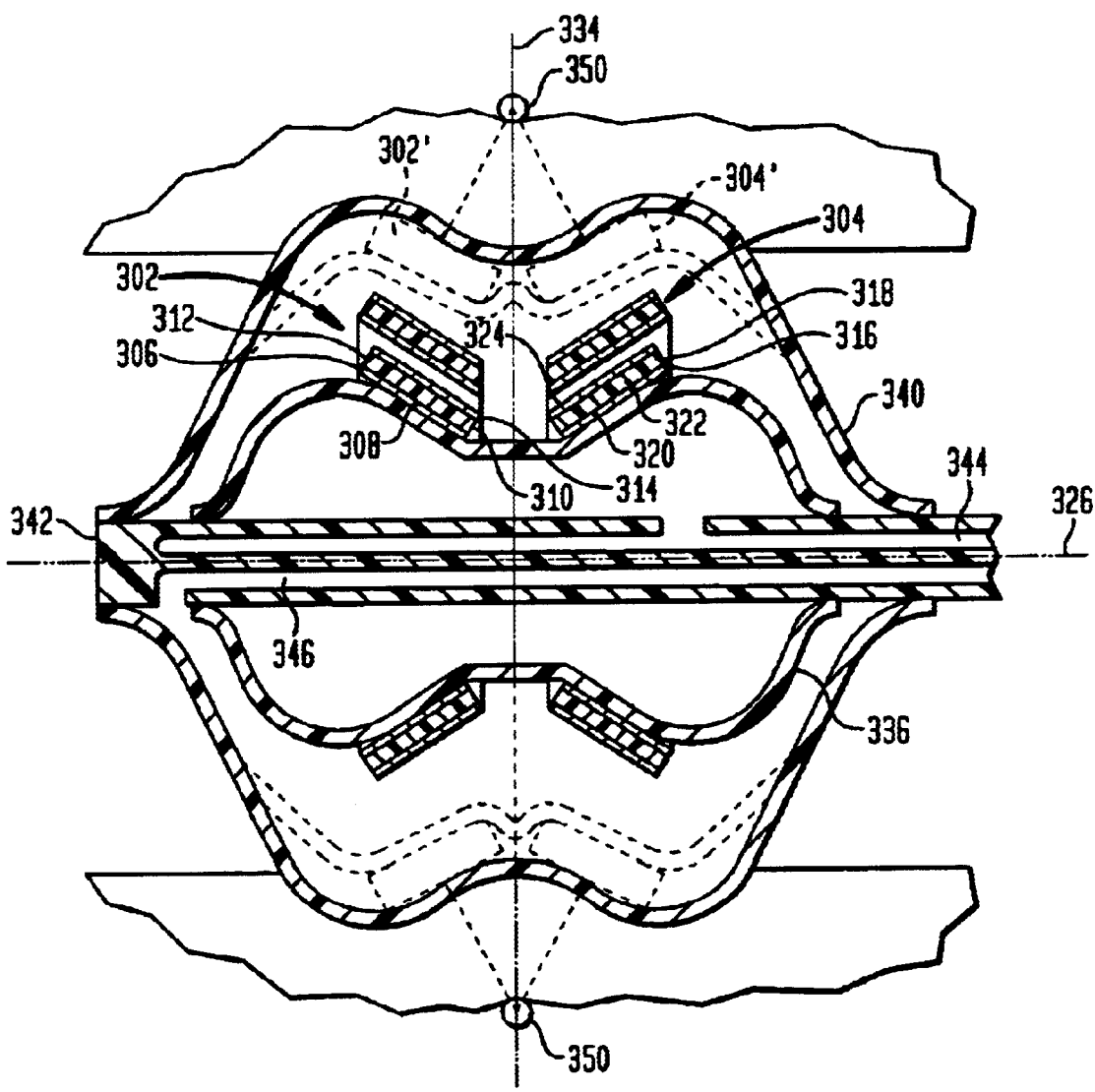
FIG. 5 is a fragmentary sectional view depicting a catheter incorporating the emitting element of FIG. 4.

A sonic emitter 300 (FIGS. 4 and 5) includes two elements 302 and 304. Element 302 includes an elongated, resilient strip 306 formed from a resilient, electrically conductive material such as stainless steel. Strip 306 has a first major surface 310 and a second major surface 308. A layer 312 of a flexible piezoelectric film such as polyvinylidene fluoride (PVDF) overlies the first surface 310 of the strip, and an electrically conductive, flexible electrode layer 314 overlies the surface of the piezoelectric material remote from strip 306. The thickness of electrode layer 314 is greatly exaggerated for clarity of illustration. In practice, this electrode may be a silk-screened layer of a conductive ink or other thin, conductive layer. Electrode layer 314 and strip 306 are electrically connected to leads (not shown) so that an alternating potential may be applied between these electrodes to excite the piezoelectric film and cause it to emit sonic energy. That is strip 306 acts as an additional electrode layer for the film. Although only a single layer of piezoelectric film is illustrated in FIG. 5, plural layers of film and plural electrode layers may be provided. The layers of piezoelectric film are interspersed between the electrode layers. As taught in copending, commonly assigned U.S. Provisional Patent Application No. 60/125,676 filed Mar. 22, 1999, [attorney docket number Trans 3.8-0211 ] the disclosure of which is hereby incorporated by reference herein, the plural layers can be excited together so that their sonic vibrations reinforce one another. Other aspects of deformable transducers suitable for use within the body are disclosed in copending, commonly assigned U.S. Provisional Patent Application No. 60/118,432 filed, Feb. 2, 1999 [attorney docket number Trans 3.8-0131 ] the disclosure of which is hereby incorporated by reference herein. The construction of element 304 is substantially identical to that of element 302. Thus, element 304 has a resilient strip 316 with first major surface 318, second major surface 320 and piezoelectric film 322 overlying the first major surface. An electrode layer 324 overlies the surface of film 322 remote from strip 316.

Each of the elongated, striplike elements 302 and 304 is wound into a generally spiral configuration about a common central axis 326. As best seen in FIG. 4, striplike element 302 has an inner end 328 closest to axis 326, and an outer end 330 remote from the axis. As shown in both FIGS. 4 and 5, the major surfaces of strip 306 lie at an angle to central axis 326, so that strip 306 has a generally conical configuration. Stated another way, the outwardly-facing surfaces correspond to a surface generated by a straight-line generatrix oblique to the central axis 326 moving in a spiral path around the axis and outwardly from the axis. Thus, the first major surface 308 faces radially outwardly, away from central axis 326, and also faces in a first axial direction (to the right in FIG. 5). The turns of the spiral element 302 overlap one another adjacent the outer end 330 of the spiral. The piezoelectric film 312 desirably extends along the first major surface from the outer end of the helix at least into the region of overlap, so that a substantial portion of the inner turn in the overlap region bears the piezoelectric film. The other sonic element 304 has the same configuration except that the direction of inclination of the strip is opposite to that of element 304. Thus, the first major surface 318, and hence the overlying piezoelectric film 322, face radially outwardly and face axially in a second direction (to the left as seen in FIG. 5). Spiral elements 302 and 304 are disposed on opposite sides of an imaginary medial plane 334 extending transverse to the central axis 326, and positioned so that the first major surfaces of the elements face axially toward this medial plane.

A flexible balloon 336, referred to herein as the expansion balloon, is disposed inside the spiral elements 302 and 304. A further balloon 340, referred to herein as the cover balloon, is disposed outside of the spiral elements. The balloons and elements are mounted to an elongated catheter body 340 adjacent the distal end thereof, with the common central axis 326 of the spiral elements extending substantially coaxially with the axis of elongation of the catheter body. The catheter body has a passage 344 communicating with the interior of expansion balloon 336 and has a separate passage 346 communicating with the interior of cover balloon 340.

In a method according to a further embodiment of the invention, expansion balloon 336 is initially deflated, and elements 302 and 304 are in the contracted position illustrated in solide lines in FIGS. 4 and 5. The distal end of the catheter is advanced through the circulatory system of the patient until it reaches the location where ablation is to be performed, such as the opening of a pulmonary vein. Cover balloon 340 is inflated with a fluid such as a saline solution to expand it into engagement with the interior wall W of the circulatory vessel. The expansion balloon is inflated within the cover balloon, so that the expansion balloon forces the turns of spiral elements 302 and 304 radially outwardly, to the expanded position illustrated in broken lines at 302' and 304' in FIG. 5. As the turns of the spiral elements are forced outwardly, the spirals unwind slightly, reducing the degree of overlap between the turns of spiral element 302 adjacent outer end 330 (FIG. 4) and likewise reducing the degree of overlap of the turns in element 304. However, even in the expanded condition, there remains some overlap between the turns. Also, the region of element 302 covered by the piezoeletric film 312 extends at least to the point of overlap between the outer turn and the inner turn, and desirably beyond this point. Thus, even in the expanded condition the piezoelectric film entirely encircles the central axis. Element 304 is in the same condition.

While the elements are in the expanded condition, they bear upon the interior wall W of the circulatory vessel through the cover balloon 340. A drive signal is applied to each piezoelectric film, causing it to emit sonic energy. The sonic energy from element 302 is directed radially outwardly, away from axis 326, and is also directed axially, in the first direction towards medial plane 334. The energy from element 304 is directed in a similar but opposite pattern, radially outwardly and in the second direction (to the left as seen in FIG. 5) toward the medial plane. Thus, the sonic vibrations from the two elements reinforce one another in a ring-like zone 350 encircling axis 326 on the medial plane 334. After the tissue in this zone has been ablated, the expansion balloon is deflated, and the sonic elements 302 and 304 return to the contracted condition, whereupon the catheter may be withdrawn or relocated.

Figure 3:
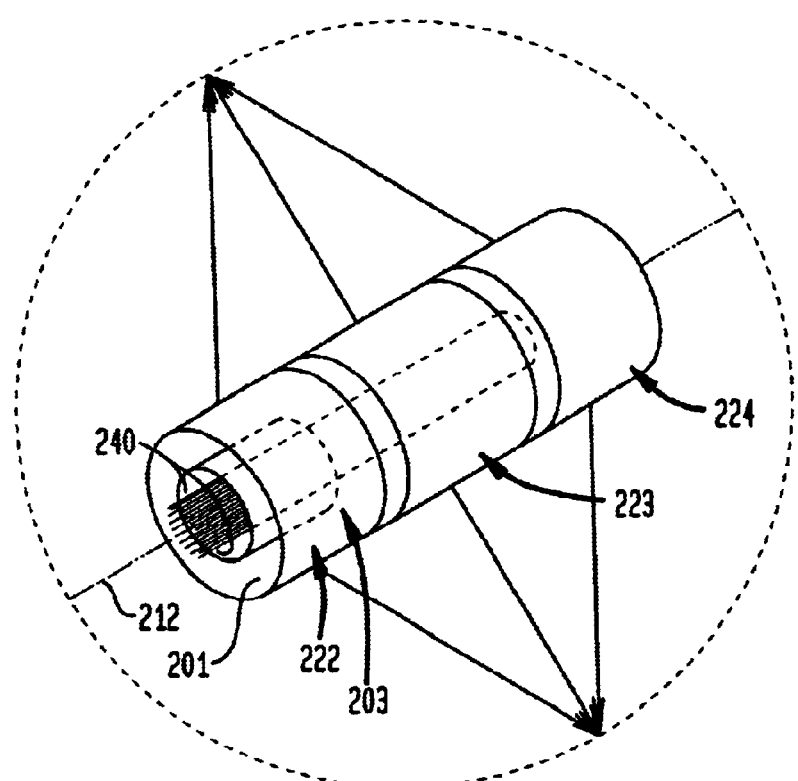
FIGS. 3 and 4 are views similar to FIG. 2 but depicting emitting elements in accordance with other embodiments of the invention.
Figure 6:
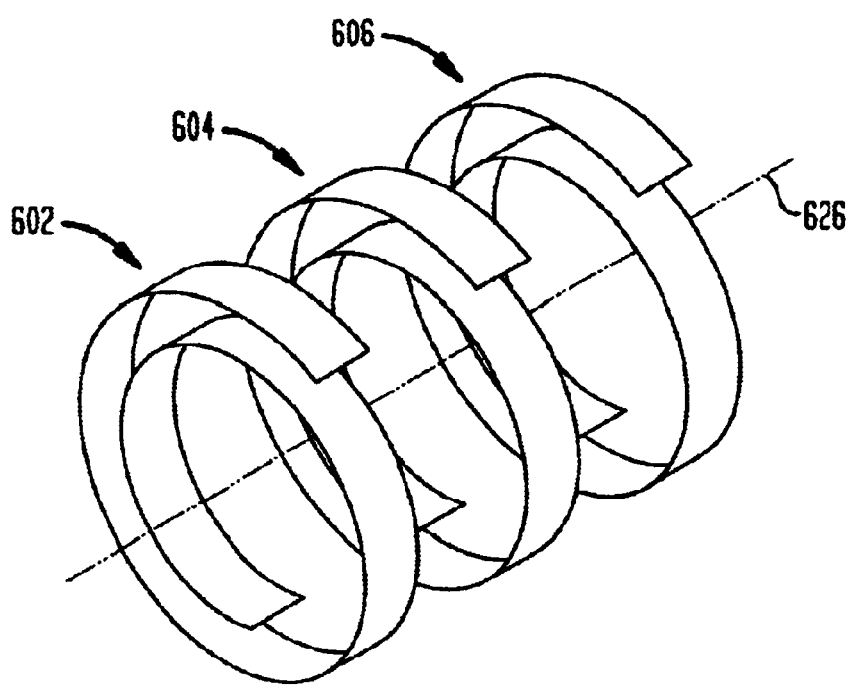
FIG. 6 is a diagrammatic perspective view depicting an emitting element in accordance with a further embodiment of the invention.

In a further variant, an ultrasonic emitting assembly includes a plurality of spiral elements 602, 604, 606 (FIG. 6). These elements are generally similar to the spiral elements 302 and 304 discussed above with reference to FIGS. 4–5. However, the outwardly-facing surfaces of helical elements 602,604 and 606 are not inclined with respect to the axis. Stated another way, the outwardly-facing surfaces correspond to a surface generated by a straight-line generatrix parallel to the central axis 626 moving in a spiral path around axis 626 and outwardly therefrom. These emitting elements are associated with balloons and catheter structure similar to that discussed with reference to FIG. 5, and can be employed in substantially the same way. The sonic vibrations applied to elements 602 and 606 may differ from those applied to the middle element, so as to provide a focusing effect similar to that discussed above with reference to FIG. 3.

Figure 7:
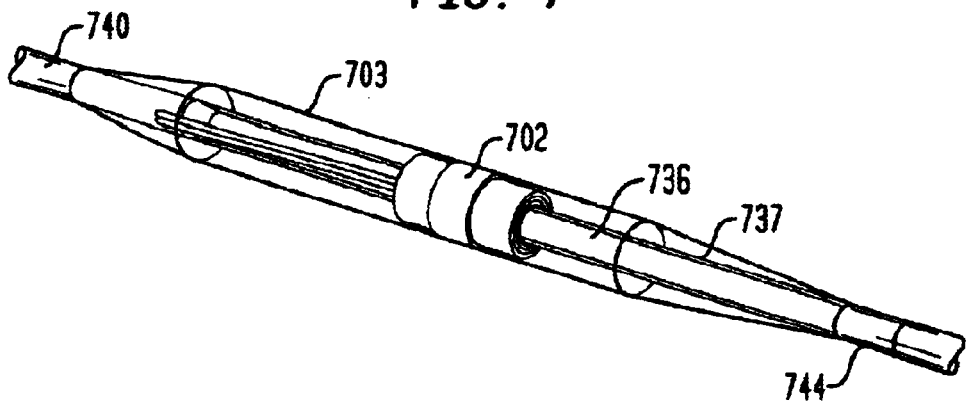
FIGS. 7, 8, 9 and 10 are diagrammatic perspective views depicting a catheter and emitting element according to yet another embodiment of the invention at different stages during operation.
Figure 8:
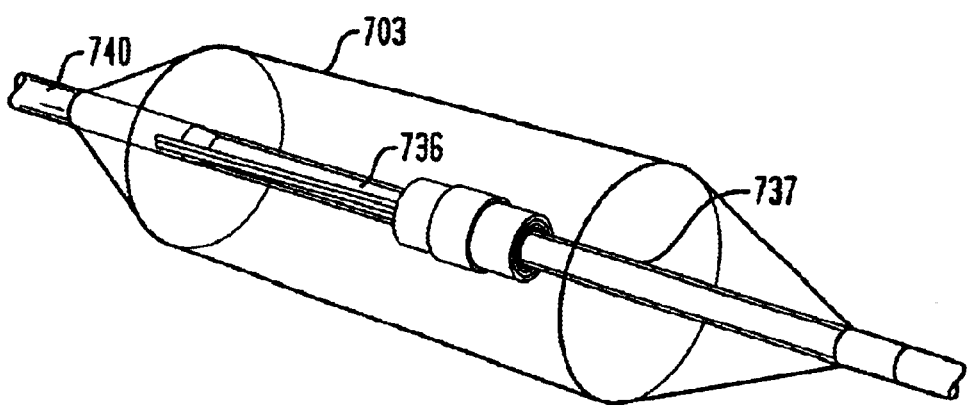
Figure 9:
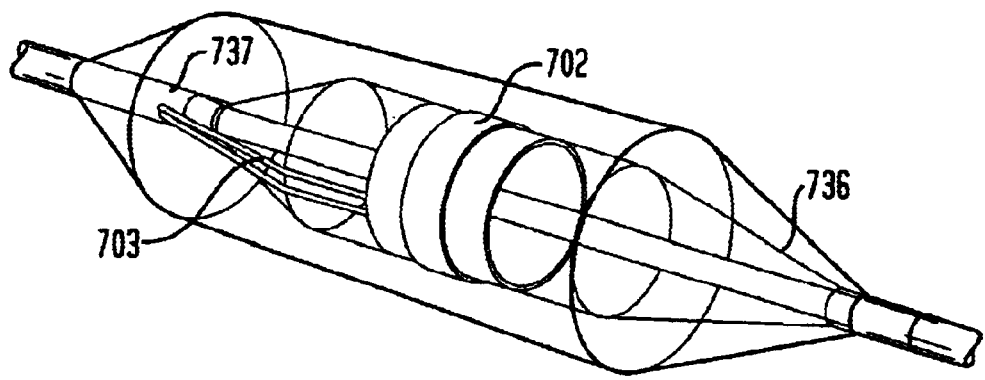
Figure 10:
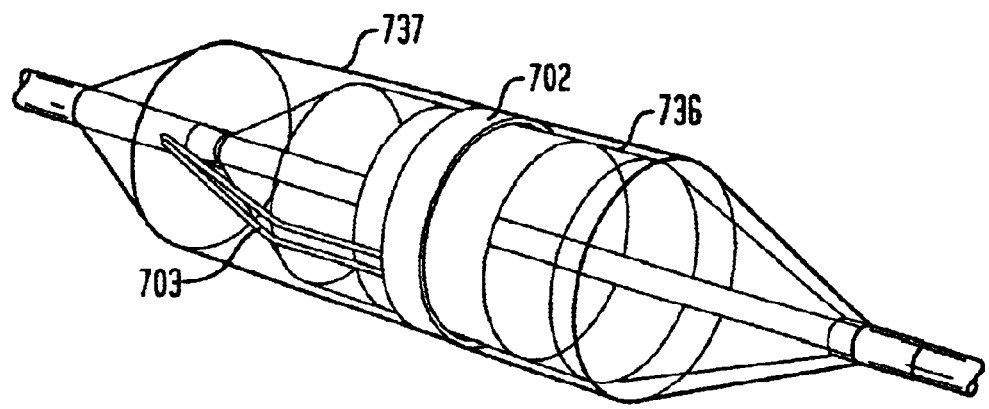

As shown in FIGS. 7–10, a sonic element 702, which may be similar to the elements discussed above, may be expanded by an inner balloon 736 disposed inside of the sonic element. An outer balloon 737 covers the sonic element and the inner balloon. Separate bores (not shown) extend through the catheter 740 to the proximal end so that each balloon can be inflated and deflated separately by external fluid pressure devices (not shown) connected at the proximal end. Wires 703 extend between the outer balloon and the inner balloon to the sonic element; these wires may be replaced by flexible conductors on the exterior surface of the inner balloon. The distal end of catheter is advanced into position within the patient with both balloons deflated and with the sonic element in its contracted position as illustrated in FIG. 7. After the catheter is in position, the outer balloon is inflated (FIG. 8). During this procedure, the inner balloon 736 may remain deflated. After the outer balloon has been inflated, the inner balloon 736 is progressively expanded as shown in FIG. 9, and the spiral transducer 702 is expanded along with it. This process continues until the spiral transducer 702 is fully expanded and bears against the outer balloon 737 and the outer balloon bears on the surrounding tissue. This provides a low impedance sonic path between the transducer and the tissue. In this condition, the transducer is ready to perform the ablation procedure discussed in the prior application. Following ablation, the balloons are deflated, typically deflating the inner balloon first and allowing the transducer to return to its original, contracted condition whereupon the outer balloon is deflated and the assembly returns to the configuration illustrated in FIG. 7. In this condition, the assembly is withdrawn from the patient or moved to a new location.

Figure 11:
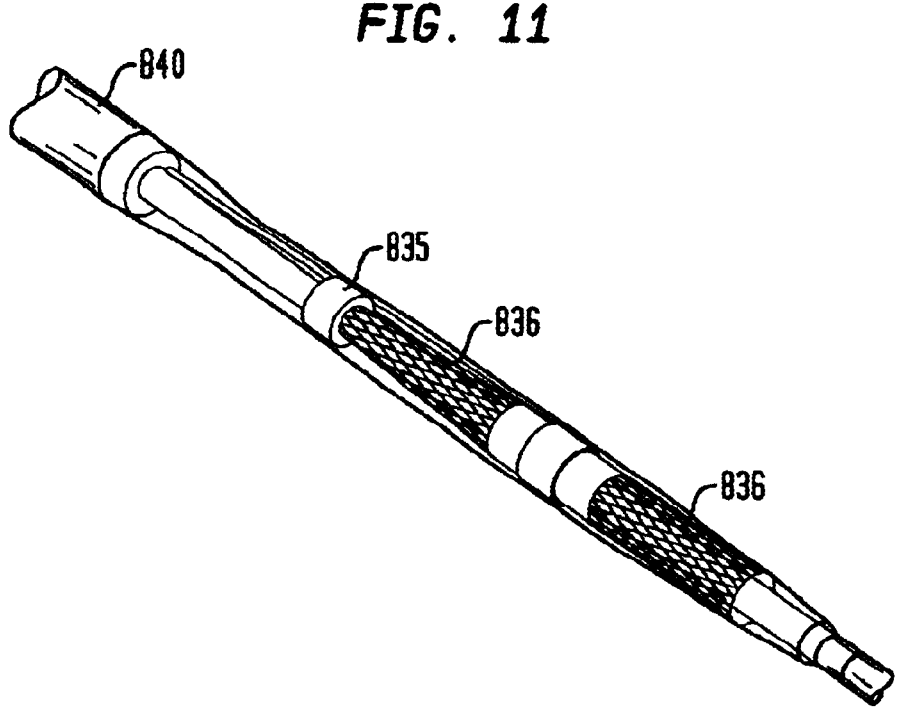
FIGS. 11 and 12 are views similar to FIGS. 7–10 depicting a catheter and emitting element according to a further embodiment of the invention.
Figure 12:
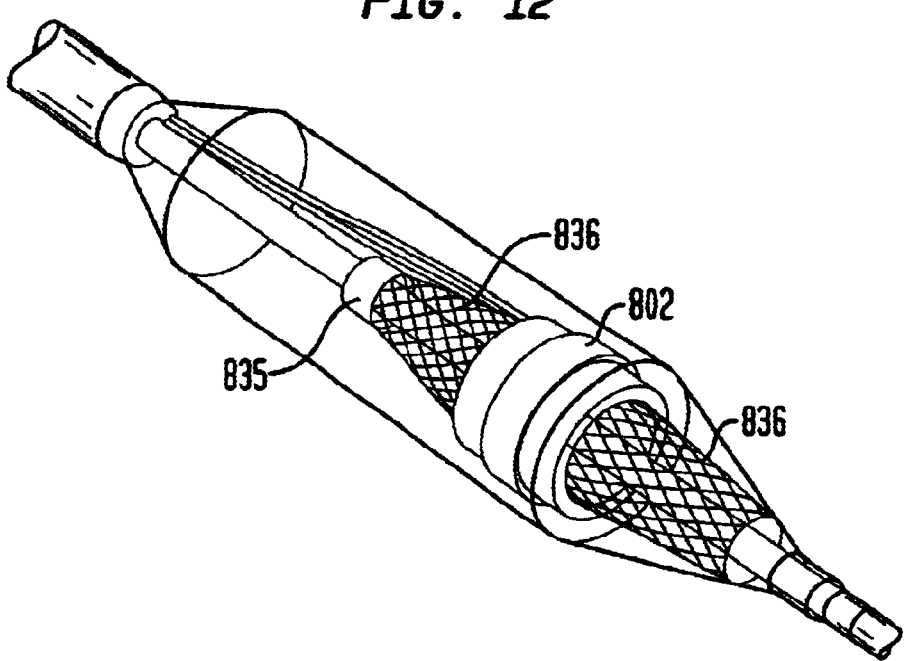

The catheter illustrated in FIGS. 11 and 12 is similar to that discussed above with reference to FIGS. 7–10 except that the inner balloon is replaced by a braid 836 which can be collapsed axially (in the direction along the axis of catheter 840) so as to expand it radially, and vice versa. After inflation of the inner balloon, a collar 835 bearing on the braid is advanced axially relative to the catheter so as to collapse the braid axially and expand it radially, thereby forcing the spiral transducer 802 outwardly as seen in FIG. 12. Here again, the spiral transducer is expanded outwardly into engagement with the outer balloon so as to provide a low impedance sonic path to the surrounding tissues. Following ablation, the braid, transducer and outer balloon are returned to their original condition (FIG. 11). In the depicted embodiment movement of the collar toward the distal end expands the braid. The positions of the components can be reversed so that movement of the collar towards the proximal end expands the braid. A wire or rod disposed in the catheter may move the collar.

Although the invention has been described above with reference to ablation of blood vessel walls, the same techniques can be used to ablate ring-like regions around other tubular anatomical structures. For example, catheters as describe above can be introduced into the urethra and the sonic element can be actuated to ablate a ring-like region within the prostate gland.

As these and other variations and combinations of the features discussed above can be utilized without departing from the present invention, the foregoing description of the preferred embodiments should be taken by way of illustration rather than by way of limitation of the invention.

What is claimed is:

1. A sonic emitting element comprising a piezoelectric element having a radiating surface in the form of a surface of revolution of a generatrix about a central axis, said generatrix including a minimum point at a minimum distance from said central axis, a first portion sloping away from the axis in a first axial direction from said minimum point, and a second portion sloping away from said central axis in a second axial direction from said minimum point.

2. An element as claimed in claim 1, wherein said first and second portions of said generatrix are curved.

3. An element as claimed in claim 2, wherein said first and second portions of said generatrix are segments of a circle, whereby said radiating surface is in the form of a portion of a toroidal surface.

4. An element comprising a piezoelectric element having a radiating surface in the form of a portion of a toroidal surface having a central axis, said portion of said toroidal surface facing outwardly away from said central axis, whereby said emitting element will focus emitted sonic energy in a generally circular band surrounding the element.

5. An element as claimed in any of claims 1, 2, 3 and 4 wherein said piezoelectric element is formed from a polymeric piezoelectric material.

6. An element as claimed in claim 1 wherein said piezoelectric element has a maximum diameter of about 1 cm or less.

7. A catheter comprising an element as claimed claim 6, and an elongated catheter body having a proximal end, a distal end and a longitudinal axis extending between said ends, said element being mounted to said body remote from said proximal end so that said central axis of said element is substantially parallel with the longitudinal axis of the catheter body.

8. A catheter as claimed in claim 7, further comprising a balloon surrounding said element and said catheter.

9. A catheter as claimed in claim 8, wherein said balloon is substantially in the form of a surface of revolution about the longitudinal axis of the catheter.

10. A method of treating tissue within the body of a subject comprising the steps of:

(a) threading a catheter into a circulatory system of the subject so that a emitting element carried on said catheter is positioned within a circulatory vessel with a central axis of the emitting element substantially aligned with an axis of the circulatory vessel, said emitting element having an axial length in a direction along said central axis;

(b) actuating said emitting element to emit sonic energy in a pattern which is generally symmetrical about said central axis, said sonic energy being emitted so that the sonic waves from different portions of said emitting element intersect and mutually reinforce one another in a ring-like focal region surrounding said central axis, said focal region having an axial length less than the axial length of said emitting element.

11. A method as claimed in claim 10, wherein sonic energy from different portions of the emitting element along the axial extent of emitting element is directed at different angles to the central axis of the radiating element.

12. A method as claimed in claim 10 wherein said actuating step is performed for a time sufficient to ablate tissue in said focal region.

13. A method as claimed in claim 12 wherein tissue disposed outside of said focal region is not ablated.

14. A method as claimed in claim 10 wherein said circulatory vessel is a blood vessel communicating with a chamber of the heart and wherein the emitting element is disposed adjacent the juncture of such blood vessel and the heart.

* * * * *

UNITED STATES PATENT AND TRADEMARK OFFICE
CERTIFICATE OF CORRECTION

PATENT NO. : 6,669,655 B1 Page 1 of 1
DATED : December 30, 2003
INVENTOR(S) : David E. Acker and Alfred Novak It is certified that error appears in the above-identified patent and that said Letters Patent is hereby corrected as shown below:

Column 1,
Line 9, "disclosure" should read -- disclosures --.
Line 9, "is" should read -- are --.

Column 2,
Line 8, insert -- the -- before "entire".
Line 58, insert -- as -- before "one".

Column 5,
Line 53, "3.8-0211" should read -- 3.8-021 --.
Line 60, "3.8-0211" should read -- 3.8-021 --.

Column 6,
Line 44, "solide" should read -- solid --.

Column 8,
Line 48, insert -- one -- before "of".
Line 54, insert -- in -- before "claim".

Column 9,
Line 2, "a" should read -- an --.

Signed and Sealed this

Sixteenth Day of March, 2004

JON W. DUDAS
*Acting Director of the United States Patent and Trademark Office*